United States Patent [19]

LaDow

[11] Patent Number: 4,778,454
[45] Date of Patent: Oct. 18, 1988

[54] SYRINGE LOADING FIXTURE

[76] Inventor: Charles R. LaDow, 340 Monroe St., Conneaut, Ohio 44030

[21] Appl. No.: 938,462

[22] Filed: Dec. 4, 1986

[51] Int. Cl.$^4$ .............................................. A61M 5/00
[52] U.S. Cl. .................................... 604/208; 604/407; 141/27
[58] Field of Search .............. 604/407, 207, 208, 210, 604/218, 232; 141/26, 27

[56] References Cited

U.S. PATENT DOCUMENTS

| | | | |
|---|---|---|---|
| 3,610,241 | 10/1971 | Le Marie | 604/407 |
| 3,840,011 | 10/1974 | Wright | 604/407 |
| 4,219,055 | 8/1980 | Wright | 604/407 |
| 4,489,766 | 12/1984 | Montada | 604/407 |
| 4,623,344 | 11/1986 | Eriksson | 604/407 |
| 4,675,018 | 6/1987 | Harden | 604/407 |

Primary Examiner—John D. Yasko
Attorney, Agent, or Firm—Ralph Hammar

[57] ABSTRACT

A fixture for loading a syringe from a vial of liquid which is of particular value to those with poor (or no) vision, the fixture being characterized by a gauge for measuring the quantity of air to be injected into the vial prior to loading and the quantity of liquid to be loaded into the syringe.

5 Claims, 1 Drawing Sheet

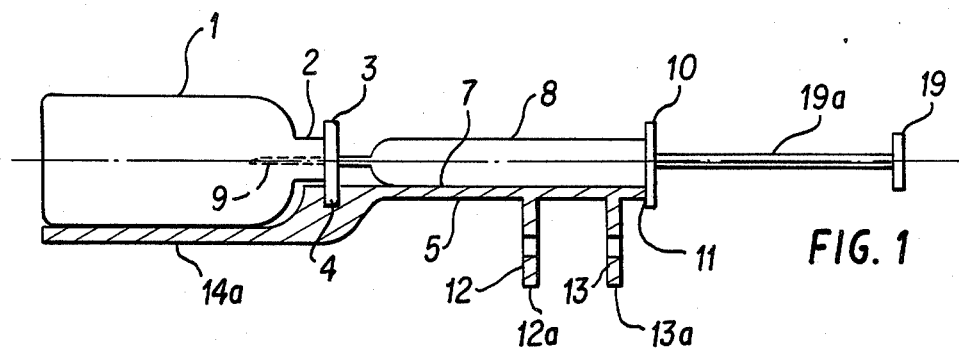
FIG. 1
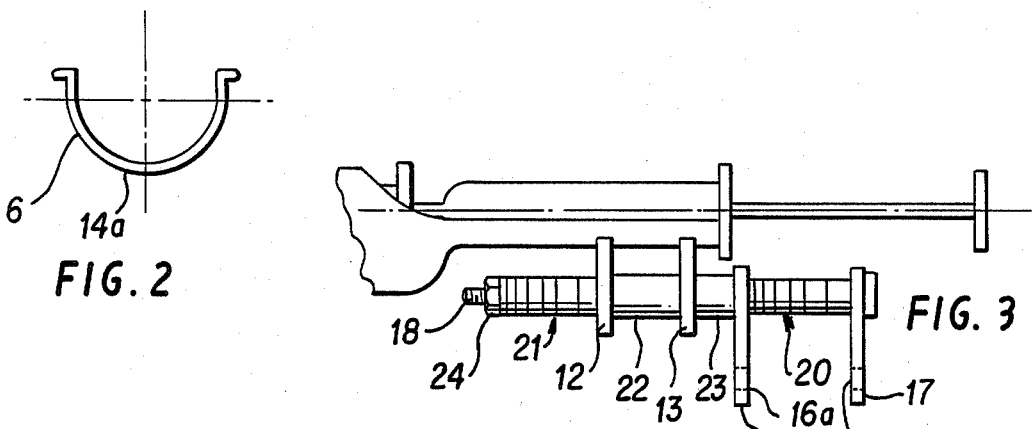
FIG. 2
FIG. 3
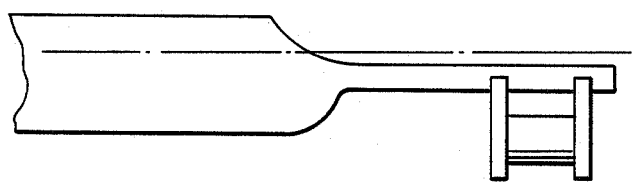
FIG. 4
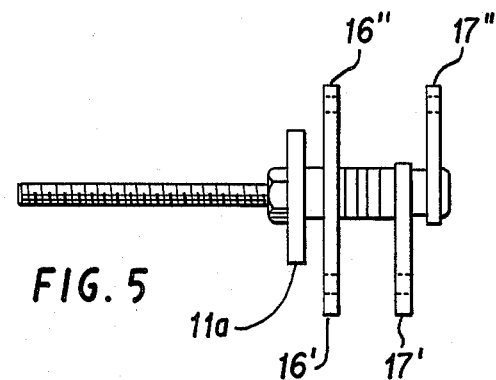
FIG. 5

SYRINGE LOADING FIXTURE

This invention is intended to simplify the loading of syringes and is particularly designed for people who are blind or who have poor eye sight. A blind person using this fixture can load an insulin syringe as fast or faster than a person with normal eye sight without the aid of this fixture.

In the drawings, FIG. 1 is a sectional side elevation of the fixture with a syringe in position to start loading, FIG. 2 is an end view, FIG. 3 is a top plan view of the fixture.

FIG. 4 is a view of the vial holder,

FIG. 5 is a view of a gauge element with two settings, each setting being usable separately.

In the drawing 1 indicates a standard medicine containing vial having a neck 2 with a metal sealing ring 3 at the center of which is a puncturable rubber seal (not shown). The sealing ring 3 is seated in a groove 4 in a holder 5 which locates the position of the front end of the vial and the back end of the vial is gripped by a clip 6 integral with the holder. The front end of the holder has a arcuate supporting surface 7 receiving a syringe 8 with its needle 9 in alignment with the axis of the medicine vial 1. The needle penetrates through the rubber seal into the interior of the vial when a rim or projection 10 at the back of the syringe is stopped against the back end 11 of the holder 5 or against locating flange 11a of FIG. 5. On the underside of the holder are hinge supports 12, 13 which with bottom surfaces 12a, 13a in alignment (coplanar) with the surface 14a at the ront of the holder 5.

The charge to be loaded into the syringe is controlled by gauge members 16, 17 rotatably mounted on hinge pin 18 extending through the gauge members 16, 17 and support numbers 12, 13. Gauge member 16 lies against the outer or back end of the rim 10 of the syringe. Gauge member 17 lies against the inner surface of plunger (handle) knob 19 for moving the syringe plunger. The space between the gauge members is controlled by the stack 20 of washers. The thickness of the stack 20 is increased by adding washers to the stack 20 from the stack 21. The thickness of the stack of washers 20 is decreased by subtracting washers from the stack 20 and adding the subtracting washers to the stack 21. The washers vary in thickness and can easily be identified by the sense of touch rather than requiring the sense of sight. The space between the supports 12, 13 is controlled by fixed bushing 22. The space between the support 13 and the gauge member 16 is controlled by bushing 23 with or without washers 23a. The length of the bushing 23 is selected so that the gauge member 16 bears against the outer surface of the rim 10 of the syringe. When the stacks of washers 20 and 21 have been adjusted to obtain the proper spacing between the gauge member 16, 17, the adjustment is locked in place by locking the nut 24 on the hinge pin 18. In the structure shown the hinge pin is screw threaded so lock nuts are used to clamp the stacks of washers 20, 21 without interfering with the rotation of the gauge members. When the nut 24 is removed, the unit carrying the gauge members 16, 17 slides out of the supports 12, 13 as in FIG. 5.

In the use of the device, the vial 1 is first loaded onto the holder 5 with the metal ring 3 seated in groove 4 and the body of the vial gripped between clamping arms 6. The piston of the empty syringe is retracted by pulling outward on the handle 19 and piston rod 19a is laid in notches 16a, 17a in gauge members 16, 17 with the rim 10 of the syringe bearing against the side 16b of gauge member 16 remote from the gauge member 17. The knob 19 is pushed inward until stopped against the surface of gauge member 17 remote from the gauge member 16. The syringe now contains the quantity of air to be injected into the vial 1 before filling the syringe. The syringe is now laid on the arcuate support surface 7 and moved toward the rubber sealing element within the metal ring 3 until the rim 10 of the syringe stops against the back end 11 of the holder or against locating flange 11a of FIG. 5. In this position, the inner end of the needle 9 completely penetrates the rubber sealing element and enters the liquid in the vial. The syringe plunger is now pushed inward to expel air through the needle into the vial to aid in the subsequent withdrawal of liquid. This continues until the plunger 18 stops against the rim 10 of the syringe. Now by holding the device upright with the vial inverted and uppermost the plunger is retracted by pulling the knob 19 outward until more than enough liquid has been withdrawn from the vial 1 into the syringe. With the knob 19 in the extended position, the gauge members 16, 17 are now swung up into position with the gauge member 16 engaging the piston rod 19a and the outer surface of the rim 10 of the syringe and the gauge member 17 engaging the piston rod 19a. Now while still holding the device in the upright position with the vial 1 inverted and uppermost, the plunger knob is pushed inward until it strikes the outer surface of gauge element 17. This discharges air and excess liquid back into the vial. The syringe is now loaded, air free and ready for use. While the injection site is being prepared, the fixture with the syringe can be rested on any horizontal surface and will not roll away. As soon as the injection site is prepared, the gauge members 16, 17 are swung clear, the syringe is lifted out of the fixture and the injection made in the usual manner.

FIGS. 4 and 5 add to the structure of FIGS. 1–3 (1) an adjustable stop 11a which can occupy positions beyond the end 11 of the holder and thereby permit the loading of longer syringes and (2) two sets of gauge members 16', 17' and 16", 17" which allow use of the fixture for two different loadings.

What is claimed is:

1. A fixture having a means for holding a vial with a puncturable seal, gauge members pivoted on said fixture, said gauge members having a first position with means for supporting a syringe in a first position in laterally spaced relation to and out of alignment with said vial and with its plunger pulled outward by its handle to fill the syringe with air, said gauge members in their aforesaid first position being in thrust relation between said handle and said syringe in its aforesaid first position so that when said handle is pushed inward until stopped by said gauge members air in excess of the volume of liquid to be loaded into the syringe is expelled, said fixture having means for supporting said syringe filled with air equal to the volume of liquid to be loaded into the syringe in a second position with the longitudinal axis of the syringe in alignment with the longitudinal axis of the vial end with said syringe being slidable toward said puncturable seal and stopped when its needle punctures said seal and establishes communication between the syringe and the liquid in said vial through said needle so the syringe may be filled by first pushing the syringe plunger inward to expell into the vial the air previously loaded into the syringe and then pulling the syringe plunger outward to overfill the syringe with liquid and then moving the gauge members from said first position to a second position in thrust relation between the handle and syringe and while holding the vial inverted and uppermost and pushing the plunger inward until stopped by said gauge members to discharge air and excess liquid back into the vial.

2. The fixture of claim 1 in which the fixture has means for mounting the gauges on a longitudinal axis spaced from and parallel to the longitudinal axis of the vial.

3. The fixture of claim 1 in which the gauge members are hinged to said fixture on a longitudinal axis spaced from and parallel to the longitudinal axis of the vial.

4. The fixture of claim 3 in which the gauge members are mounted on a hinge pin and are adjustable spaced from each other by washers on said pin.

5. The syringe of claim 1 having a plurality of sets of said first and second gauge members, each set having a spacing corresponding to a different loading of liquid into the syringe.

* * * * *